(12) United States Patent
Epstein

(10) Patent No.: US 7,849,612 B2
(45) Date of Patent: Dec. 14, 2010

(54) ORTHOTIC DEVICE

(76) Inventor: Merel Epstein, 27895 Berrywood La., #75, Farmington Hills, MI (US) 48334

( * ) Notice: Subject to any disclaimer, the term of this patent is extended or adjusted under 35 U.S.C. 154(b) by 646 days.

(21) Appl. No.: 11/897,330

(22) Filed: Aug. 30, 2007

(65) Prior Publication Data

US 2008/0060229 A1   Mar. 13, 2008

Related U.S. Application Data

(63) Continuation-in-part of application No. 09/603,222, filed on Jun. 26, 2000, now Pat. No. 7,272,900, which is a continuation of application No. 09/096,946, filed on Jun. 12, 1998, now Pat. No. 6,098,319.

(51) Int. Cl.
*A61F 5/14* (2006.01)

(52) U.S. Cl. .................. 36/159; 36/155; 36/43; 36/71

(58) Field of Classification Search ............. 36/37, 36/81, 173–174, 176, 178, 180, 140–142, 36/71, 43–44, 155–159, 85; 428/64.1, 65.2, 428/66.2, 66.4, 66.5; 411/458, 537, 538
See application file for complete search history.

(56) References Cited

U.S. PATENT DOCUMENTS

| | | | | |
|---|---|---|---|---|
| 3,432,376 A | * | 3/1969 | Lythgoe et al. | 156/234 |
| 5,399,404 A | * | 3/1995 | Laughlin et al. | 428/41.3 |
| 5,840,783 A | * | 11/1998 | Momchilovich et al. | 522/112 |
| 6,270,872 B1 | * | 8/2001 | Cline et al. | 428/40.1 |
| 6,485,826 B1 | * | 11/2002 | Watanabe et al. | 428/343 |
| 7,097,892 B2 | * | 8/2006 | Sano | 428/40.1 |

* cited by examiner

*Primary Examiner*—Jila M Mohandesi
(74) *Attorney, Agent, or Firm*—The Weintraub Group, P.L.C.

(57) ABSTRACT

An adhesive strip for use with a balancing disc for balancing the gait of the user comprises a medial polyester sheet having an upper surface and a lower surface. An acrylic adhesive is the disposed on both the upper and lower surfaces. A silicone release sheet is disposed atop the upper layer of acrylic adhesive and a circular polyester sheet is disposed over the lower layer of adhesive. The overlying polyester sheet is scored to facilitate removal of at least a portion thereof in order to expose a portion of the acrylic adhesive for immediate adherence to a surface of an associated balancing disc. After emplacement, the other portion of the polyester sheet is removed to secure the adhesive to the disc. When the silicone release sheet is removed, the disc can then be readily applied to an insole or to a footwear item.

6 Claims, 2 Drawing Sheets

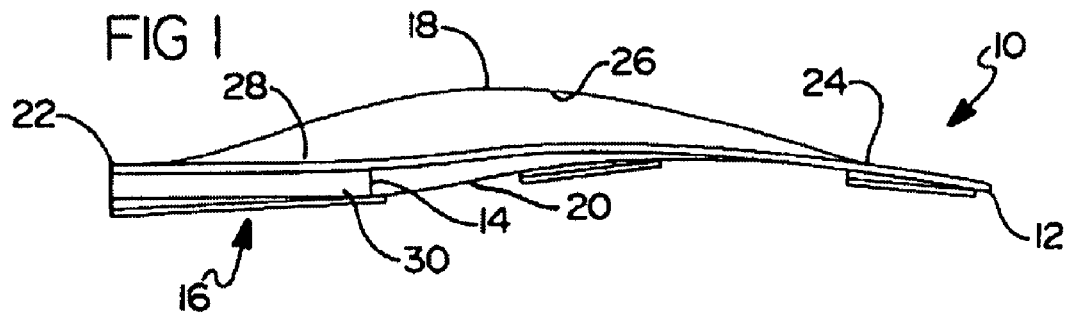
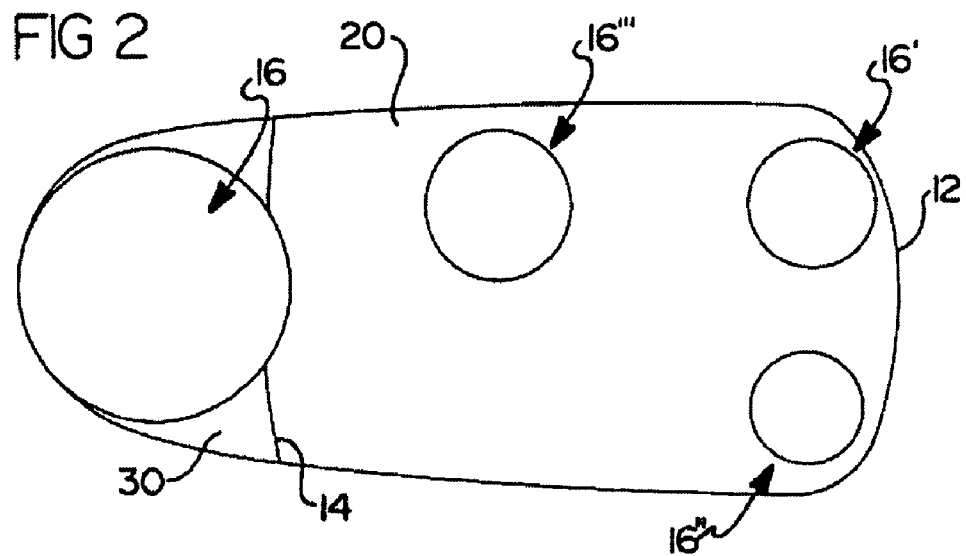
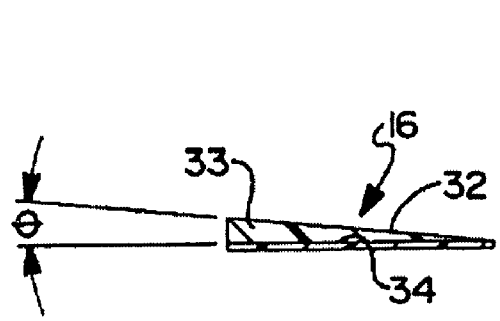
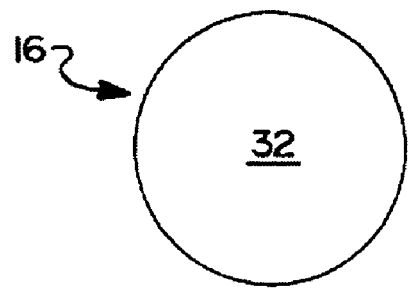

ORTHOTIC DEVICE

CROSS-REFERENCE TO RELATED APPLICATIONS

This application is a Continuation-In-Part application of co-pending U.S. patent application Ser. No. 09/603,222 filed Jun. 26, 2000; now U.S. Pat. No. 7,272,900 which in turn, is a continuation application of U.S. patent application Ser. No. 09/096,946 filed Jun. 12, 1998, now U.S. Pat. No. 6,098,319, that issued on Aug. 8, 2000, the entire disclosures of both are hereby incorporated by reference.

BACKGROUND OF THE INVENTION

1. Field of the Invention

The present invention involves the field of orthotic foot devices used in podiatry, chiropractics, physical therapy, orthopedics, osteopathy, and general health care. More particularly, the present invention concerns a balancing disc for use with footwear items, such as sandals, shoes, insoles and the like and an improved adhesive strip for securing the balancing disc to the footwear item.

2. Prior Art

Orthotic foot devices, or "orthotics", are used as inserts into footwear to give a user enhanced biomechanical balance and weight distribution during both standing and ambulation. Orthotic foot devices may be either medically prescribed to a precise configuration or an "off the shelf" item which are emplaced within a shoe or other footwear items. Typically, such orthotics comprise a plate in the shape of a plantar part of a human foot plus optional additions, such as wedges, which are secured to the plate, anterior or posterior or both, to create proper alignment and balance of skeletal and muscular body components, thereby providing enhanced balance and weight distribution to the user.

Heretofore, in practice, once installed in a footwear item in attempting to effect proper balance and weight distribution, a skilled technician or practitioner usually would make adjustments to either or both the posterior and anterior areas of the orthotic devices by emplacement of wedges in correct orientation. This is a time consuming task, because of the minute corrections necessary to be made. It is to be, thus, appreciated that there has not been a simple and convenient way for making these necessary adjustments.

A balancing disc or appliance for use with an insole or the like in balancing the gait of a user is disclosed in U.S. Pat. No. 6,098,319, issued Aug. 8, 2000 to Epstein, the Applicant herein, as well as in co-pending U.S. patent application Ser. No. 09/603,222, filed Jun. 26, 2000, the entire disclosures of which are specifically incorporated herein by reference. The balancing disc thereof provides for balance and weight distribution adjustment, and is easily integrated with existing orthotic foot devices as well as into other footwear items or devices. The balancing disc is wedge-shaped, generally circular, and securable to an orthotic device or directly to the footwear item in a plurality of incremental orientations through a 360°. It is securable in both the posterior and anterior portions of an orthotic foot device to provide the requisite adjustment for effecting proper balance and weight distribution. As noted, the balancing disc may be used in conjunction with insoles, orthotics or may be directly attached to a footwear item such as a shoe, sandal, etc.

While suitable for the purposes there intended, there is an ongoing need for improvements. In particular, there is an ongoing need to provide improved positional stability of the orthotic device relative to the foot structure and during ambulation. For example, because many people have abnormal weight distribution, the foot places different loads on the orthotic device. While the aforementioned wedge-shaped disc is adapted to be placed in any desired angle, maintenance of that secured placement, under loads placed thereon by the foot, is critical in maintaining balance.

SUMMARY OF THE INVENTION

According to a first aspect hereof, there is provided a foot device for balancing the gait of a user including a balancing disc, the device having an upper surface adapted to support the foot of a user, and a lower surface, the balancing disc including an adhesive strip for securing the balancing disc to the shoe engaging lower surface of the shoe insole.

The adhesive strip is a thin, flexible, multilayered strip and comprises a central or medial sheet of polyester sandwiched between upper and lower layers of an acrylic adhesive, a silicone-treated release sheet is disposed atop said upper layer of acrylic adhesive and a lower release sheet of a scored polyethylene removably covers the lower layer of acrylic adhesive. Removal of the release sheets enables the lower layer of acrylic adhesive to be adhered to the lower surface of the foot device and the upper layer of acrylic adhesive to be adhered to the balancing disc.

The balancing disc, per se, comprises a substantially wedge-shaped member for balancing the gait of a user and the multilayered adhesive strip having the silicone release sheets removed therefrom. The disc has a bottom surface for engaging the shoe and a top surface juxtaposed with and secured to the lower surface of a footwear item, such as an insole, orthotic or to the undersurface of a shoe or sandal interior liner, the multilayered adhesive strip comprising the central sheet of polyester sandwiched between upper and lower layers of an acrylic adhesive, the lower layer of acrylic adhesive being adhered to the top surface of said disc, and the upper layer of acrylic adhesive being adhered to the footwear item.

The top and bottom surfaces of the balancing discs hereof are angularly inclined with respect to each other. Each disc has its top surface and bottom surface angularly inclined with respect to each other by an angle $\Theta$, which angle generally, ranges from about 2° to about 6°.

The angular inclination enables compensation for balance, depending upon a user's foot.

Ordinarily, the disc hereof is placed upon a heel portion of an orthotic device or an insole, but may be placed directly inside and over the heel or other portion of a shoe or in another position on the orthotic device or insole.

Also, a plurality of the devices hereof may be disposed on the footwear item at appropriate positions.

The present disc device may be made from any suitable material, such as a rigid or semi-rigid leather, metal, rubber, synthetic resinous material, plastic, rigid polymer or the like.

Also, from a commercial standpoint, a plurality of these discs may be packaged as a kit with the discs being of the same or differing in their angles of inclination between the top and bottom surfaces thereof or combinations thereof.

According to another aspect hereof, a kit for balancing the gait of a user comprises a plurality of discs and corresponding adhesive strips for attaching the discs to a footwear item, each disc comprising a substantially rigid, circular wedge member having a planar upper surface and a planar lower surface, the upper and lower surfaces being angularly inclined with respect to each other by an angle of about 2° to about 6°, the upper surface being attachable to a footwear item and positionable in any angle to enable incremental rotational balancing adjustment for imparting proper weight distribution and balance to the user, wherein the discs have different angles of inclination, and wherein each adhesive strip includes upper and lower adhesive layers corresponding substantially to an associated disc for adhesively securing the upper and lower surfaces of the disc, respectively, to the disc and the footwear item.

According to this invention, the adhesive strips are separately provided, wherein each strip includes removable upper and lower release sheets, wherein the removal exposes the adhesive layers to enable attachment of the balancing disc to the footwear.

For a more complete understanding of the present invention, reference is made to the following detailed description and accompanying drawing. In the drawing, like reference characters refer to like parts throughout the several views, in which:

BRIEF DESCRIPTION OF THE DRAWING

FIG. 1 is a side view of an orthotic foot device deploying the balancing disc of the present invention;

FIG. 2 is a bottom view of the orthotic foot device of FIG. 1 with the disc in place;

FIG. 3 is a side view of the disc hereof;

FIG. 4 is a top plan view of the disc hereof; and

DETAILED DESCRIPTION OF THE EMBODIMENTS

Figure 5:
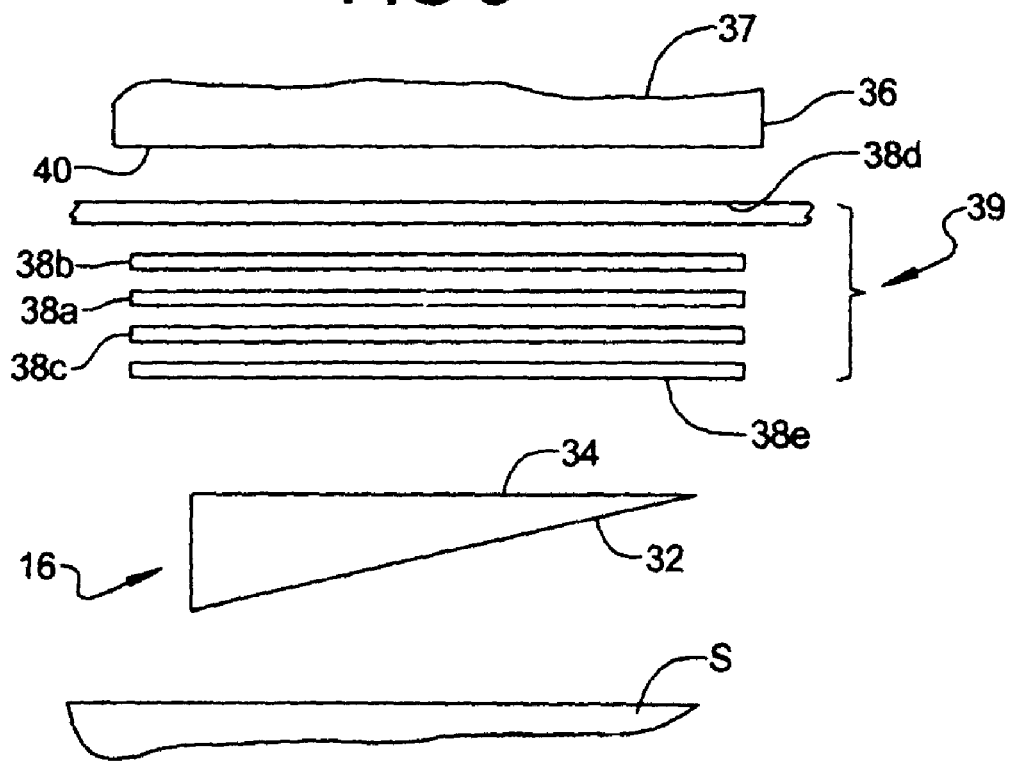
FIG. 5 is an exploded section view of an adhesive strip according to this invention being deployed with an insole.

With more particularity, and with reference to the drawing, there is depicted an orthotic foot device or orthotic device, generally, denoted at 10, having a balancing disc of the present invention secured thereto and which is, generally, denoted at 16.

In a preferred utilization hereof, the present invention is used with either an extrinsically posted heel cup orthotic device or a flat heel cup orthotic device. Both the flat heel cup type and posted heel cup type of devices are well-known and commercially available, one source being sold under the trademark EVER-FLEX by Ever-Flex, Inc. of Taylor, Mich.

Additionally, the present disc may be used on an intrinsically anterior portion or an extrinsically posted orthotic device, both laterally and/or medially of either an intrinsically or extrinsically posted device. Clearly, the disc hereof may be used for both the anterior and posterior portions of the orthotic device, as needed. Likewise, the present invention may be deployed on a flat insole or may be directly emplaced within a footwear item, such as a shoe, sandal, etc.

As shown in the drawing, and with reference to the utilization of the disc hereof in conjunction with an orthotic device, and as is known to those skilled in the art to which the present invention pertains, the typical orthotic device 10 includes a plate or sole plate 12 made of a flexible rigid or semi-rigid material, such as a foam, leather, steel, plastic or the like. Herein for illustrative purposes, the orthotic device has an intrinsically posted heel cup portion depicted in the drawing. As shown, the plate 12 has a first or top or foot-engaging surface 18 and a second or bottom or footwear-engaging surface 20 opposite the first surface 18. The plate 12 and, particularly, the first surface 18 thereof is shaped to the sole of a human foot, with curvatures, as appropriate. The plate 12 comprises a posterior portion 22, an anterior portion 24, and an arch portion 26 between and connecting the posterior portion 22 and the anterior portion 24.

Clearly, the disc hereof may be used for both the anterior and posterior portions of the device, as needed and may be used for either the left or right foot.

In use, a post 14, made of any suitable rigid, flexible or semi-flexible material, as required, including synthetic rubber, foam, etc., and the like, may be secured to the second or bottom surface 20 of the plate 12 about the posterior portion 22. The post 14 has a first surface 28 and a second surface 30 opposite the first surface. The first surface 28 is shaped to snugly overlie the posterior portion 22 of the plate 12 at the second surface 20 thereof. The second surface 30 of the post 14 is, usually, substantially flat or planar. The post 14 is attached to the plate 12 at the posterior portion 18 thereof by any suitable means, such an adhesive or the like.

As noted above, heretofore, if the plate 12 and/or a combination of the plate 12 and the post 14 did not effect the desired result, minute adjustments were accomplished with rectangular-shaped shims or wedges or similar devices. The present disc 16 obviates this, as detailed below.

The balancing disc 16 hereof is a substantially circular solid wedge member made of either rigid, semi-flexible or flexible material, such as plastic, rubber, synthetic rubber or the like, as required, prescribed and/or desired.

The balancing disc 16 has a first surface 32, a second surface 34, opposite the first surface 32, and a side wall 33 integrally formed with the first surface 32 and the second surface 34. The first surface 32 and the second surface 34 are each substantially circular planar surfaces. The first surface 32 is angularly inclined with respect to the second surface 34 by an angle $\Theta$, which generally ranges from about 2° to about 6°. Thus, the disc 16 defines a circular wedge or shim.

The first surface 32 of the disc 16 may be attached to either the post 14 or the plate 12, or both, by any suitable means, such as an adhesive or the like. Because the disc 16 is circular, it may be universally rotated through a 360° arc, to provide the minute adjustments prerequisite for imparting proper weight distribution and balance to the user. Similarly, and as shown in FIG. 2, one or more discs 16 may be deployed on the plate and/or the heel cup portion of the orthotic 10 to provide the necessary adjustment for a particular user. For example, one disc 16 may be deployed on the posterior portion and one or more discs 16', 16", etc., on the anterior portion. The locations and orientations of discs 16 on a given plate 12 and/or heel cup portion are determined on a case-by-case basis by a skilled practitioner, based on the balancing needs of an individual user. The disc 16 may, likewise, have any suitable diameter as dictated by the orthotic device 10 and/or post 14 to which it is to be secured. Similarly, in a commercial form, the present disc 16 may be packaged as a kit wherein a plurality of discs have varying angles of inclination between the prescribed ranges.

As noted hereinabove, the present disc may be disposed directly on a footwear item, also, by placing it inside a shoe, sandal, etc., at the appropriate position or on a planar insole.

Further, the present device or disc may be used in conjunction with a biomechanical device such as an ankle brace, a foot brace, a combined ankle and foot brace and the like, where stabilization of the heel is required. The device hereof may be directly incorporated into such a brace with provision for access thereto for adjustment being provided, or may be used as a separate element in conjunction therewith.

Figure 6:
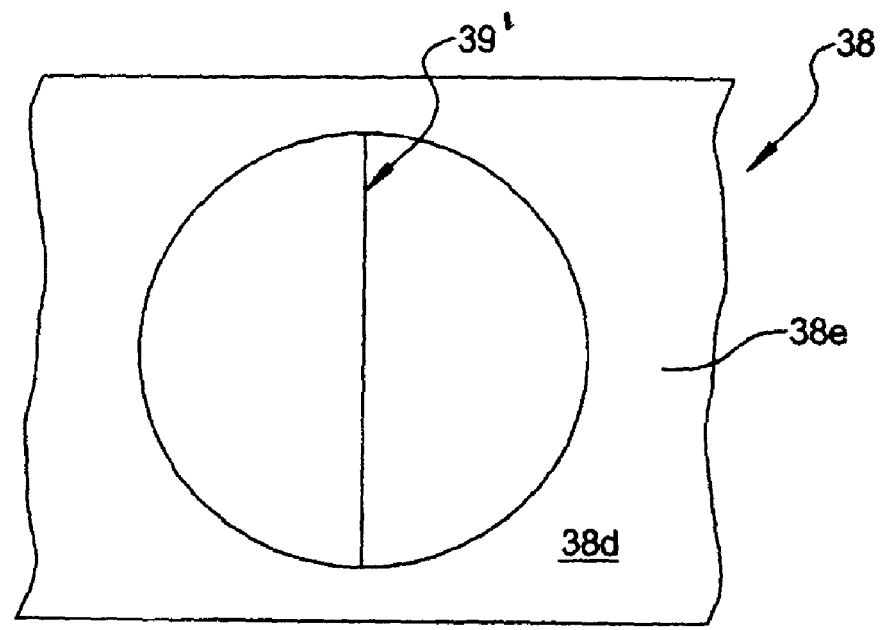
FIG. 6 is a partial top view of the strip hereof.

Referring to FIGS. 5 and 6, the balancing disc 16 is illustrated for use with a shoe insole 36, which insole is fittable inside a shoe, generally, indicated by the reference numeral "S", the insole having an upper surface 37 adapted to support the foot of a user, and a lower surface 39, adapted to seat against the shoe. According to an important aspect of this invention, an adhesive strip 38 is provided for securing the balancing disc 16 to the shoe engaging lower surface 39 of the shoe insole 36.

The adhesive strip 38, preferably, comprises a plurality of thin, flexible, multi-layered circular elements 39 (only one of which is shown). Each element 39 comprises a central sheet 38a of polyester material sandwiched between upper and lower layers of an acrylic adhesive 38b and 38c. These acrylic adhesives are well-known and commercially available. A layer 38d of a silicone-treated release sheet is disposed atop the upper layer 38b of acrylic adhesive. As noted, this silicone release sheet, preferably, accommodates a plurality of circular elements placed thereon or it may be a single circular sheet associated with a single element 39.

A circular die cut-thin film polyethylene sheet 38e removably covers the lower or opposite layer 38c of acrylic adhesive. The die-cut sheet 38e, as shown, enables a portion of the adhesive layer 38c to be exposed when the sheet 38e is peeled along the score line 39' thereof to enable attachment of the disc to an insole or other orthotic. After placement at the appropriate spot, the other portion of the sheet 38e is removed to expose the rest of the adhesive layer 38c to fix the disc in position. In other words, removal of the release sheets 38d and 38e exposes and enables one layer of acrylic adhesive to be adhered to the lower surface 40 of the insole 36 and the other adhesive layer of acrylic adhesive to he adhered to the surface 34 of the balancing disc 16.

The acrylic adhesive is more compatible with materials commonly utilized in fabrication of insoles, and, thus, during ambulation, the adhesive resists movement of the balancing disc from the desired angular and position relative to the anterior and posteriors ends of the insole.

As noted, a plurality of balancing discs may be sold in kit form, with each of the discs or, preferably, pairs of discs having a different angle, in the range noted hereinabove. The kit of discs 16 may also be sold with a single or a pair of insoles or orthotics 36.

Additionally, the kit may be include a corresponding plurality of adhesive strips 38, which the user may apply when and where desired to a balancing disc 16 having the desired angle. Furthermore, the adhesive strips may be pre-applied to the balancing disc 16, leaving to the user the step of removing the upper removal strip 38 and attachment of the lower surface 39 of the insole 38.

Having, thus described the invention what is claimed is:

1. In a balancing disc of the type for balancing the gait of a user when used in conjunction with a footwear item, the improvement comprising:
    (a) substantially rigid, circular, rotatable wedge member having a continuous planar upper surface and a continuous planar lower surface, the upper and lower surfaces being angularly inclined with respect to each other by an angle θ of about 2° to about 6° the disc being attachable to a footwear item for imparting proper weight distribution and balance to the user,
    (b) an adhesive strip for affixing the disc to a footwear item, the adhesive strip including:
        (1) a circular element having a central sheet of polyester,
        (2) an upper layer of acrylic adhesive disposed atop the central sheet,
        (3) a lower layer of acrylic adhesive disposed on the lower surface of the central sheet,
        (4) a removable silicone treated release sheet disposed atop the upper layer of acrylic adhesive, and
        (5) a scored polyethylene sheet overlying the lower layer of acrylic adhesive, the score line enabling partial removal of the sheet to expose a portion of the lower adhesive layer.

2. The improvement of claim 1 wherein the disc is formed of a substantially non-compressible solid material selected from the group consisting of a rigid plastic, leather, rubber and a synthetic resinous material.

3. A kit for use in balancing the gait of a user comprising: a plurality of circular balancing discs, each disc having an upper surface and a lower surface, the first surface being angularly inclined with respect to the second surface by an angle which generally ranges from about 2° to about 6°, and a plurality of adhesive strips, each strip being associated with a disc, each circular adhesive strip comprising:
    (1) a circular element having a central sheet of polyester,
    (2) an upper layer of acrylic adhesive disposed atop the central sheet,
    (3) a lower layer of acrylic adhesive disposed on the lower surface of the central sheet,
    (4) a removable silicone treated release sheet disposed atop the upper layer of acrylic adhesive, and
    (5) a scored polyethylene sheet overlying the lower layer of acrylic adhesive, the score line enables partial removal of the sheet to expose a portion of the lower adhesive layer.

4. The kit of claim 3 which further comprises at least one insole, at least one of the discs being affixable to the insole.

5. The kit of claim 3 which comprises: a plurality of pairs of discs wherein each of the pair has a different angle of inclination with respect to any other disc pair within the kit.

6. The kit of claim 3 wherein the silicone release strip has a length and width greater than the diameter of any disc, the kit further comprising:
    a plurality of circular adhesive elements being disposed along the length of the silicone treated release sheet.

* * * * *